United States Patent [19]

Knifton et al.

[11] Patent Number: 4,565,896
[45] Date of Patent: Jan. 21, 1986

[54] PROCESS FOR LOW PRESSURE SYNTHESIS OF ETHYLENE GLYCOL FROM SYNTHESIS GAS

[75] Inventors: John F. Knifton, Austin; Roger G. Duranleau, Georgetown, both of Tex.

[73] Assignee: Texaco Inc., White Plains, N.Y.

[21] Appl. No.: 663,284

[22] Filed: Oct. 22, 1984

[51] Int. Cl.$^4$ .................. C07C 29/00; C07C 31/20
[52] U.S. Cl. ................................... 568/852; 568/678; 568/680; 568/881
[58] Field of Search .............................. 568/852

[56] References Cited

U.S. PATENT DOCUMENTS 4,356,332  10/1982  Knifton .......................... 568/852
4,362,820  12/1982  Kaplan .......................... 518/700

FOREIGN PATENT DOCUMENTS 90522  5/1983  Japan .

Primary Examiner—J. E. Evans
Attorney, Agent, or Firm—Jack H. Park; Kenneth R. Priem; Cynthia L. Kendrick

[57] ABSTRACT

This invention relates to the manufacture of ethylene glcyol and more particularly to a low pressure process for making ethylene glycol comprising reacting synthesis gas, i.e. a mixture of carbon monoxide and hydrogen, plus formaldehyde in the presence of a homogeneous liquid catalyst containing an effective amount of cobalt-containing compound and a silicon or germanium-containing promoter and a solvent at a temperature of at least 50° C. and a pressure of at least 500 psi wherein said ethylene glycol product separates as a separate liquid phase from the solvent.

15 Claims, No Drawings

PROCESS FOR LOW PRESSURE SYNTHESIS OF ETHYLENE GLYCOL FROM SYNTHESIS GAS

This application is related to U.S. Ser. Nos. 663,281, 663,280 and 663,602, (Agent's Docket Nos. 80,362, 80,401 and 80,402) filed of even date.

FIELD OF THE INVENTION

This invention relates to a new process for preparing ethylene glycol. More particularly, this invention relates to a novel low pressure process for preparing ethylene glycol from syngas which comprises contacting syngas, a mixture of carbon monoxide and hydrogen, plus formaldehyde or paraformaldehyde with a catalyst comprising a cobalt-containing compound and a halogen-free silicon or germanium-containing promoter solubilized in certain classes of solvents at a temperature of at least 50° C. and a pressure of from about 500 psig wherein the system allows ease of separation of the glycol products from the main body of solvent.

BACKGROUND OF THE INVENTION

Ethylene glycol is a chemical which has found wide use in industry. It is used, for example in the preparation of plasticizers for vinyl polymers and as a component in polyester fibers and antifreeze formulations. In view of its many uses, there is a need to find new and more economical methods for preparing ethylene glycol.

Proposed methods for making ethylene glycol involve the reaction of carbon monoxide with hydrogen in the presence of various proposed catalyst systems at elevated temperatures and pressures. For example, one of the earliest disclosed processes for making polyhydroxy compounds from readily available and inexpensive starting materials such as formaldehyde, carbon monoxide and hydrogen was disclosed in U.S. Pat. No. 2,451,333. The process comprised heating the starting materials with a reduced cobalt oxide hydrogenation catalyst under a high pressure, in excess of 100 atm. and at a temperature from about 80° C. to 300° C. Actually the examples in this patent used high pressures in the range of 500–800 atmospheres.

In Japan Kokai No. 76,128,903 (1976) to Mitsubishi a procedure is disclosed for preparing ethylene glycol by the reaction of CO, $H_2$ and HCHO with a cobalt catalyst containing a trivalent P, As or Sb compound at a temperature of about 160° C. and a pressure of about 180 Kg/cm$^2$, or approximately 2700 psi.

Similarly U.S. Pat. No. 4,144,401 uses CO, $H_2$ and formaldehyde as starting materials, but they are reacted in the presence of an alcohol solvent and a catalytic amount of rhodium or a rhodium-containing compound at a moderate temperature and pressure. Of course use of rhodium in a catalyst makes it expensive for commercial purposes. Methanol is also produced in substantial amounts in this process.

U.S. Pat. No. 4,356,332 pertains to the production of ethylene glycol by reaction of formaldehyde with carbon monoxide and hydrogen in the presence of a catalyst comprising a cobalt-containing compound and a tin-or germanium-containing promoter and in the presence of a substantially inert, oxygenated hydrocarbon solvent.

In U.S. Pat. No. 4,200,765 there is disclosed a process for preparing glycol aldehyde by reacting formaldehyde, hydrogen and carbon monoxide in an aprotic solvent at elevated temperatures and superatmospheric pressures in the presence of a rhodium catalyst with subsequent conversion of the glycol aldehyde to ethylene glycol by hydrogenation.

Japan Kokai No. 82,118,527 (1981) to Mitsubishi discloses the use of a ruthenium-based catalyst with a trivalent phosphorous compound to convert formaldehyde, CO and H into ethylene glycol. The selectivity to ethylene glycol is not specified.

Japan Kokai No. 82,130,940 (1981) to Mitsui Petrochemicals employs a rhodium compound and an alkali metal compound. Again selectivity to ethylene glycol is not specified.

In U.S. Pat. No. 4,362,820 only carbon monoxide and hydrogen, without formaldehyde are used as starting materials for conversion to ethylene glycol via a catalyst comprising a cobalt-containing compound and a large excess of organosilicon compound. In most of the examples an operating temperature range of 250°–270° C. is employed, coupled with pressures of about 4000–8000 psi. Weight ratios of ethylene glycol to methanol were typically Ca. 2:1. Here selectivity to glycol cannot be calculated because only the yields of MeOH and glycol are specified.

Additional Japanese applications disclose the use of a solution of formalin, carbon monoxide and hydrogen to produce ethylene glycol in the presence of a cobalt catalyst. See Japanese Application No. 197909 to Agency of Ind. Sci. Tech. In Jap. Application No. 188137 to the same agency, ethylene glycol is produced by reacting CO and hydrogen optionally with formaldehyde in the presence of a cobalt carbonyl and a phenol and/or alkylphenol.

Japanese Application No. 004782 (1981) to Mitsubishi discloses a process for producing ethylene glycol from formaldehyde, CO and $H_2$ in the presence of a catalyst containing ruthenium and a trivalent organo-phosphorous compound.

Finally in Japan Kokai Tokyo Koho JP No. 57,130,933 to Mitsubishi, acetals are reacted with CO and H in the presence of a cobalt-iodine catalyst system to produce ethylene glycol.

Many of these processes require the use of high pressures (particularly in the absence of an added formaldehyde source), some use expensive rhodium-containing compounds, in most the selectivities for ethylene glycol are not very substantial, and there is difficulty in separation of the glycol products from the selected solvent.

The disclosure of a process for producing ethylene glycol from simple starting materials such as syngas (i.e. carbon monoxide and hydrogen) and formaldehyde or paraformaldehyde by reacting the starting materials in the presence of a catalyst compound which would be relatively inexpensive even on a commercial scale, where reaction could be conducted at low temperatures and pressures, which would provide for better selectivity to desired ethylene glycol and its derivatives, and which would allow for ease of separation of glycol products from the solvent would be an advance in the art.

SUMMARY OF THE INVENTION

This invention concerns a process for making ethylene glycol comprising contacting a mixture of synthesis gas, i.e., carbon monoxide and hydrogen plus, formaldehyde with a catalyst comprising a cobalt-containing compound and a silicon or germanium-containing compound in the presence of a solvent selected from the group including aromatics, halogen-containing aromatic and ether solvents, and heating the resultant mixture at a temperature of at least 50° C. and a pressure of at least 500 psi and preferably less than 5000 psi for sufficient time to produce the desired ethylene glycol and separating said glycol products from the solvent. By using this catalyst system one can obtain substantial selectivity in the formation of ethylene glycol, the process can be operated at lower temperatures and pressures, use of extreme conditions and expensive catalyst compounds required in many of the prior known processes can be avoided and separation of the glycol product from the solvent can be facilitated.

The process of the invention as far as the formation of the desired ethylene glycol is concerned may be represented by the following equation:

$$CO + 2H_2 + HCHO \rightarrow HOCH_2CH_2OH + H_2O \qquad (1)$$

Typical concentrations of ethylene glycol in the crude liquid product phase range up to 24 wt % or more and typical yields of ethylene glycol (basis formaldehyde charged) range up to 30 mole %. Total glycol products may comprise up to 37 wt % or more of the crude liquid. With toluene as solvent, the ethylene glycol concentration in the aqueous product phase is 37% and the yield of total glycol products is 55 wt %.

DETAILED DESCRIPTION OF THE INVENTION

In the operation of the process of the invention, ethylene glycol is prepared from a synthesis gas mixture of carbon monoxide and hydrogen plus formaldehyde or paraformaldehyde by a process comprising the following steps:

(a) contacting said mixture of carbon monoxide, hydrogen and formaldehyde or paraformaldehyde with a catalyst comprising a cobalt-containing compound and a silicon or germanium-containing compound solubilized in certain classes of solvents;

(b) heating said mixture to a temperature of at least 50° C. under a pressure greater than 500 psi and less than 5000 psi with sufficient carbon monoxide and hydrogen to satisfy the above-noted stoichiometry of the desired ethylene glycol synthesis until substantial formation of the desired ethylene glycol and glycol products has been achieved; and (c) separating said glycol products from the selected solvent.

In order to present the inventive concept of the present invention in the greatest possible detail, the following supplementary disclosure is submitted. The process of the invention is practiced as follows:

As noted, the new catalyst system used in the process of the invention contains a cobalt-containing compound and a silicon or germanium-containing promoter. The cobalt compound to be used may be chosen from a wide variety of organic and inorganic compounds, complexes, etc. It is only necessary that the catalyst employed contain the cobalt in any of its ionic states.

The cobalt-containing compound employed may take many different forms. For instance the cobalt may be added to the reaction mixture in an oxide form as in the case of, for example, cobalt(II) oxide, (CoO) or cobalt-(II,III) oxide ($Co_3O_4$). Alternatively, it may be added as the salt of a mineral acid, as in the case of cobalt(II) nitrate hydrate ($Co(NO_3)_2.6H_2O$), cobalt(II) phosphate, cobalt(II) sulfate, etc. or as the salt of a suitable organic carboxylic acid, for example, cobalt(II) formate, cobalt(II) acetate, cobalt(II) propionate, cobalt naphthenate, or bonded to a carbonyl-containing ligand as in the case of cobalt acetylacetonate, etc. The cobalt may also be added to the reaction zone as a carbonyl or hydridocarbonyl derivative. Here, suitable examples include dicobalt octacarbonyl, ($Co_2(CO)_8$), cobalt hydridocarbonyl, ($HCo(CO)_4$) and substituted carbonyl species such as the organophosphorus cobalt carbonyls like $HCo(CO)_3(Bu_3P)$.

Preferred cobalt-containing compounds include oxides of cobalt, cobalt salts of mineral acids, cobalt salts of organic carboxylic acids and cobalt carbonyl or hydridocarbonyl derivatives. Among these, particularly preferred are dicobalt octacarbonyl, cobalt(II) oxide, cobalt(II) nitrate, cobalt acetylacetonate and cobalt(II) acetate.

The silicon-containing promoter employed in the practice of this invention may also take many different forms. Generally, the promoter should contain at least one bond between a silicon atom and a carbon atom, but suitable organosilicon compounds may comprise mono-, di-, tri- and tetraorgano groups bonded to silicon. Each organo group may be an alkyl, aryl or aryalkyl moiety, having one to 20 carbon atoms. The silicon-containing promoter may also contain silicon-oxygen bonds, and preferred promoters are halogen-free silanes containing at least one silicon-hydrogen bond per molecule.

Typical of suitable organosilicon compounds that are suitable for use in the process of equation (1) include trialkylsilanes, such as triethylsilane ($Et_3SiH$), tricyclohexylsilane [($C_6H_{11})_3SiH$], trimethylsilane, tri-n-hexylsilane and methyldiethylsilane ($MeEt_2SiH$), as well as dimethylethylsilane and the tripropylsilanes, the dialkylsilanes such as diethylsilane ($Et_2SiH_2$) and dimethylsilane, the tetraalkylsilanes such as tetramethylsilane and tetraethylsilane, the arylsilanes such as triphenylsilane ($Ph_3SiH$), diphenylsilane and hydroxytriphenylsilane, as well as the alkoxysilanes such as triethoxysilane [$(EtO)_3SiH$], phenyltriethoxysilane, tetraethoxysilane and tetramethoxysilane. Less satisfactory are the halogenated organosilanes such as chlorotrimethylsilane, dimethylsilane chloride ($Me_2SiHCl$), chlorotriphenylsilane, dichlorodimethylsilane ($Me_2SiCl_2$), chlorotriethylsilane, and iodotrimethylsilane. Other suitable organosilicon promoters containing at least one silicon-hydride bond, and more than one silicon atom per molecule, include:

$H_3SiCH_2SiH_3$
$H_3SiCH_2CH_2SiH_3$
$CH_3SiH_2CH_2SiH_3$
$CH_3SiH_2CH_2SiH_2$
$CH_4SiH_2CH_2$

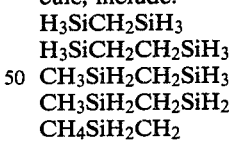

Suitable silanes containing more than one silicon-hydride bond per molecule are exemplified by:

$(CH_2=CHCH_2)_2SiH_2$

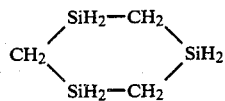

$(C_2H_5)_2SiH_2$

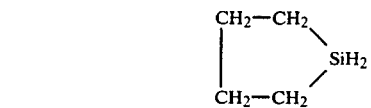

C₆H₁₃SiH₃
CH₃CH=CHCH₂SiH₃

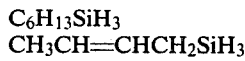

CH₂=CHCH₂SiH₃
C₆H₅CH₂CH₂SiH₃
C₆H₅CH(CH₃)SiH₃
(C₃H₇)₂SiH₂
(CH₃)(isoC₄H₉)SiH₂
(C₂H₅) (isoC₄H₉)SiH₂
(CH₂=CH)(C₂H₅)SiH₂
(CH₂=CH)(C₄H₉)SiH₂

Also effective as silicon-containing promoters in the practice of this process are siloxanes and polyalkylsiloxanes. These may include hexaethyldisiloxane, hexamethylcyclotrisiloxane, octamethylcyclotetrasiloxane, hexamethyldisiloxane, tetramethyldisiloxane (Me₂HSiOSiHMe₂), methylhydrocyclosiloxane, as well as alkylsiloxane polymers of the type:

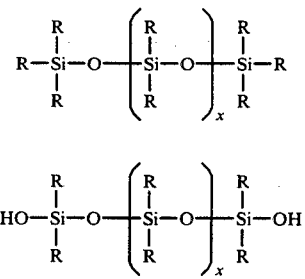

wherein R is one or different alkyl groups containing 1 to 6 carbon atoms.

Equally useful are the higher M.W. tetraalkylsilanes and tetraalkoxysilanes wherein each alkyl or alkoxy group contains 1 to 20 carbon atoms, and each alkyl group may have the same or different carbon number.

Preferred organosilane compounds include triethylsilane, triphenylsilane, trimethylsilane, diphenylsilane, tricyclohexylsilane, tetramethylsilane, tetraethylsilane, hydroxytriphenylsilane, diethylsilane and tripropylsilane.

The germanium-containing compounds which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermane, tetraethylgermane, tetraphenylgermane and tetramethylgermane, or an organohalide germanium compound such as diphenylgermanium chloride, methylgermanium trichloride, phenylgermanium trichloride, tin-n-butylgermanium iodide, triethylgermanium chloride, triethylgermanium iodide, trimethylgermanium chloride, triphenylgermanium bromide and triphenylgermanium chloride, or as an organogermanium hydride, such as triphenylgermanium hydride, or as an organogermanium oxide or carboxylate such as triphenylgermanium acetate, or as a germanium alkoxide such as germanium butoxide, germanium ethoxide and germanium methoxide.

The preferred germanium-containing promoter compounds are the organo-halide germanium compounds, the hydrocarbyl germanium compounds, and the organogermanium hydrides. Among these, particularly preferred are triphenylgermanium bromide, trimethylgermanium bromide, triphenylgermanium hydride, tetraphenylgermane, tetraethylgermane and triethylgermanium chloride.

The cobalt-containing compounds and the germanium-containing promoter may be added separately to the reaction mixture in the synthesis of the desired ethylene glycol (eq. 1), or they may be added as one or more preformed complexes. The preferred preformed complexes are the trialkyl(tetracarbonylcobalt)germanium and triaryl(tetracarbonylcobalt)germanium complexes. Illustrative examples of such performed complexes are triphenyl(tetracarbonylcobalt)germanium(IV) and trimethyl(tetracarbonylcobalt)germanium(IV). These complexes are prepared by standard literature methods such as described by D. J. Patmore and W. A. C. Graham, Inorg. Chem. 5, 981 (1967).

As characterized above, this process is operated as a homogeneous liquid phase mixture. The process is typically carried out in a solvent. The solvent should preferably be a liquid at room temperature but should at least, in part, be a liquid under the conditions of reaction. The solvent is selected such that it is capable of:

(a) Maintaining the cobalt catalyst in the homogeneous liquid phase mixture throughout the synthesis of desired ethylene glycol.

(b) Ensuring good selectivity and yields to desired ethylene glycol and its derivatives.

(c) Achieving separation of the majority of the ethylene glycol product as a separate liquid phase from the cobalt catalyst-rich solvent phase at the completion of the desired glycol synthesis.

Three classes of solvents are disclosed herein that are useful in the process of this invention and which satisfy the criteria described supra; these include aromatic hydrocarbon solvents, halogenated aromatic-containing solvents and those solvents containing both the halogen and ether functions.

Generally these solvents will contain up to 20 carbon atoms per molecule and preferably a maximum of 4 halogen atoms per molecule. The solvent must be substantially inert under typical co-hydrogenation conditions that yield glycol products and it must be one which has a normal boiling point of at least 65° C. at atmospheric pressure. Preferably, the solvent will have a boiling point greater than that of methanol and other oxygen-containing reaction products so that recovery of the glycol products by distillation is facilitated.

Suitable aromatic-type solvents that are satisfactory in the practice of this invention contain 6 to 20 carbon atoms per molecule and at least one aromatic ring moiety per molecule. They are exemplified by, but not limited to, benzene, toluene, p-xylene, o-xylene, m-xylene, mixed xylenes, ethylbenzene, mesitylene, biphenyl, cumene, diethylbenzene, diphenylmethane, dixylylethane, durene, ethyltoluenes, fluorene, naphthalene, n-nonylbenzene, phenyltoluenes, stilbene, tetralin, tetramethylbenzenes, tetraphenylmethane, and n-propylbenzene.

Preferred aromatic-type solvents include benzene, toluene, m-xylene, o-xylene, p-xylene and tetralin, as well as mixtures thereof.

Suitable halogen-containing solvents that are satisfactory for this glycol process contain up to 20 carbon atoms per molecule and preferably no more than 4 halogen atoms per molecule. They are exemplified by, but not limited to, chlorobenzene, bromobenzene, o-dichlorobenzene, 1,2,4-trichlorobenzene, 1,3,5-tribomobenzene, p-bromoltoluene, 2-bromo-m-xylene, α-bromo-p-xylene, 2-chlorobiphenyl, 7-chlorobiphenyl, o-dibromobenzene, 2,2'-dibromobiphenyl, 4,4'-dibromobiphenyl, 2,5-dibromotoluene, 2,4,6-tribromotoluene, 2,3,6-trichlorotoluene, p-xylene dichloride and 1,2,4-trifluorobenzene.

Also effective are halogenated solvents containing other substituent groups in the molecule, particularly those containing both the halogen and ether functions. Examples of such solvents include p-bromoanisole, m-chloroanisole and brominated diphenyl oxide.

The most effective solvents in terms of (a) glycol concentration in the crude aqueous phase of the liquid product, (b) total glycol product yield and (c) cobalt recovery in solution appear to be aromatics of the group including toluenes, xylenes and tetralin, and halogenated solvents of the group including o-dichlorobenzene, 1,2,4-trichlorobenzene, p-bromoanisole, m-chloroanisole, bromobenzene and dibromobenzene. There appears to be very little competing water-gas shift or methanation activity with this class of solvent-solubilized cobalt-silane or cobalt-germane catalyst. Ethylene glycol/methanol ratios may reach 3:1 or better.

The quantity of cobalt-containing compound and the silicon or germanium-containing compound to be used in the process of the invention may vary. The process is conducted in the presence of a catalytically effective quantity of the active cobalt-containing compound, the active silicon or germanium-containing compound and solvent of a particular class which gives the desired product in a reasonable yield. The reaction proceeds when employing as little as about $10^{-2}$ weight percent, and even lesser amounts of the cobalt-containing compound, together with as little as about $10^{-2}$ weight percent of the silicon or germanium-containing compound and as little as about 10 wt % solvent based on the total weight of the reaction mixture. The upper concentration is dictated by a variety of factors including catalyst cost, partial pressures of carbon monoxide and hydrogen, operating temperature, etc. A cobalt-containing compound concentration of from about $10^{-2}$ to about 30 weight percent in conjunction with a silicon or germanium-containing compound concentration of from about $10^{-2}$ to about 30 percent and a solvent concentration of from about 10 to about 95 weight percent based on the total weight of the reaction mixture is generally desirable in the practice of this invention.

Particularly superior results are obtained when the above-noted components of the catalyst system are combined as follows on a molar basis: cobalt-containing compounds to silicon or germanium-containing compounds of 1:0.1 to 1:10 (Co:Si or Ge). In contrast to the direct synthesis of ethylene glycol from synthesis gas (as for example in U.S. Pat. No. 4,362,820) normally conducted at higher pressures than in the instant work, the use of a silicon-containing compound in large excess over the cobalt-containing compound, may lead to a substantial supression of glycol yield from syngas plus formaldehyde.

The temperature range which can be employed in the process of the invention may vary over a considerable range depending upon experimental factors, including the choice of catalyst, pressure and other variables. A preferred range of operability is from about 50° C. to about 350° C. when superatmospheric pressures of syngas are employed. A narrower range of about 100° C. to 220° C. represents a particularly preferred temperature range.

The pressure employed may also vary over a considerable range, but in most cases is at least above 500 psig. A preferred operating range varies from about 1000 psig to about 5000 psig, although pressures above 5000 psig also provide useful yields of the desired product. The pressures referred to herein represent the total pressure generated by all the reactants, although they are substantially due to the carbon monoxide and hydrogen fractions. In the presence of formaldehyde or paraformaldehyde, the total pressures required for glycol syntheses using cobalt, silane or germane-promoted catalyst systems are normally lower than those pressures required for direct glycol production from $CO/H_2$ (See, for example, U.S. Pat. No. 4,367,820). This may in part be due to the fact that the formation of formaldehyde from synthesis gas (eq 2) is thermodynamically unfavorable under the range of operating conditions disclosed in these syntheses (See Stanford Research Institute Report #23A (Dec. 1978) entitled "Formaldehyde").

$$CO + H_2 \rightarrow HCHO \qquad (2)$$

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide, hydrogen and formaldehyde present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The most desired product of this synthesis, ethylene glycol (EG) will be formed in significant quantities (up to Ca. 37 wt % concentration in the crude liquid product) using the cobalt-silicon or germanium promoted catalyst system of this invention. Also formed are significant amounts of diethylene glycol (DEG), propylene glycol (PG), together with derivatives such as the ethylene glycol monoalkyl ethers (e.g. ethylene glycol monomethyl ether, (EGMME). Selectivity to total glycol products (EG+DEG+PG+ECMME) may exceed 55 wt % using toluene as the solvent. Lower monohydric alcohols, methanol and ethanol are also present in the crude liquid product mix. Each of these oxygenated products, including ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch gauge (psig).

The yield of ethylene glycol in each synthesis (mole %) is estimated basis equation 1 using the formula:

$$\frac{\text{Total Ethylene Glycol Produced (mmole)}}{\text{Total formaldehyde charged (mmole)}} \times 100$$

Total liquid yield increase (wt %) is estimated basis:

$$\frac{(\text{Liquid + Solid Product, g}) - (\text{Catalyst + Solvent + Formaldehyde Charged, g})}{(\text{Catalyst + Solvent + Formaldehyde Charged, g})} \times 100$$

To illustrate the process of the invention, the following examples are given. It is to be understood, however, that the examples are given in the way of illustration and are not to be regarded as limiting the invention in any way.

EXAMPLE I

A 450 ml capacity reactor with glass liner was charged with a mixture of dicobalt octacarbonyl (12.0 mmole Co, 2.052 g), triethylsilane (24.0 mmole Si, 2.790 g) and paraformaldehyde (0.1 mole, 3.0 g) in 1,2,4-trichlorobenzene (15.0 g). The mixture was flushed with nitrogen, the reactor sealed, flushed with synthesis gas, pressured to 2700 psig with $CO/H_2$ (1:2), and heated to 160° C. with agitation. After four hours, the reactor was allowed to cool, the gas pressure (1625 psig) noted, and the excess gas sampled and vented. 24.6 g of a two-phase liquid product was recovered, there was no solid precipitate at this stage.

Analysis (glc) of the less-dense liquid product (4 ml) shows it to contain:

24.5 wt % ethylene glycol (EG)
5.4 wt % ethylene glycol monomethyl ether (EGMME)
2.2 wt % propylene glycol (PG)
4.5 wt % diethylene glycol (DEG)
6.6 wt % methanol
0.4 wt % ethanol
31.7 wt % water
1.1 wt % 1,2,4-trichlorobenzene Analysis by glc of the heavier liquid product (16 ml) shows it to contain:

90.8 wt % 1,2,4-trichlorobenzene
0.2 wt % methanol
0.6 wt % methyl formate
0.3 wt % ethylene glycol monomethyl ether Analysis of the typical gas sample shows it to contain:

65% hydrogen
33% carbon monoxide
0.3% carbon dioxide

The ethylene glycol product and its derivatives may be recovered from the crude, aqueous-rich phase of the liquid product by fractional distillation in vacuo.

TABLE I

SYNTHESIS OF ETHYLENE GLYCOL

| Example | Catalyst Precursor[a] and Solvent | $H_2O$ | MeOH | EtOH | EGMME | EG | PG | DEG[c] | Solvent | Product[b] Phase | Proportion Total Liquid Product (%) | Liquid Yield Increase (%) |
|---|---|---|---|---|---|---|---|---|---|---|---|---|
| II | $Co_2(CO)_8Et_4Ge$ | 44.1 | 9.2 | 0.9 | | 17.4 | 3.0 | 4.3 | 0.3 | L | 25 | 9 |
|  | p-Bromoanisole | 0.8 | 0.9 | 0.1 | | 0.5 | | | 81 | H | 75 | |
| III | $Co_2(CO)_8Et_4Ge$ | 49.3 | 5.9[c] | 0.5 | 4.8 | 19.6 | 3.1 | 3.8 | 0.2 | L | 26 | 10 |
|  | p-Bromoanisole | 0.7 | 0.5 | 0.1 | 0.3 | 0.4 | 0.4 | 0.5 | 85 | H | 74 | |
| IV | $Co_2(CO)_8Et_4Ge$ | 42.6 | 7.6 | 0.7 | 5.8 | 20.3 | 2.1 | g | | L | 14 | 15 |
|  | m-Chloroanisole | 0.8 | 0.2 | | 0.2 | | | | 91 | H | 86 | |
| V | $Co_2(CO)_8Et_3SiH$ | 48.9 | 9.8 | 0.7 | 6.3 | 17.3 | 2.2 | 3.3 | 3.4 | L | 10 | 10 |
|  | p-Bromoanisole | 0.4 | 0.5 | 0.1 | 0.4 | 0.3 | 0.2 | 3.4 | 88 | H | 86 | |
| VI | $Co_2(CO)_8Et_3SiH$ | 33.2 | 12.3 | 0.6 | 7.6 | 17.9 | 1.5 | 3.5 | 4.7 | L | 15 | 6 |
|  | Bromobenzene | 0.4 | 0.6 | | 2.3 | 0.1 | 0.1 | | 91 | H | 85 | |
| VII | $Co_2(CO)_8Et_3SiH$ | 37.9 | 13.8 | 0.7 | 6.8 | 21.1 | 2.1 | 2.5 | 3.9 | L | 16 | 4 |
|  | Bromobenzene/ p-Dibromobenzene | 0.7 | 1.0 | 0.1 | 1.6 | 0.3 | 0.2 | | 55/21 | H | 84 | |
| VIII | $Co_2(CO)_8Et_3SiH$ | 30.2 | 12.8 | 0.7 | 10.2 | 20.4 | 2.0 | d | 13.1 | L | 19 | 9 |
|  | o-Dichlorobenzene | 0.8 | 0.4 | | 0.5 | 0.1 | 0.2 | | 95 | H | 81 | |
| IX | $Co_2(CO)_8Et_3SiH$ | 17.7 | 8.5 | 0.6 | 10.8 | 22.3 | 1.7 | 10.7 | 6.6 | H | 13 | 10 |
|  | Chlorobenzene | 0.3 | 1.0 | 0.1 | 1.0 | 0.5 | e | 0.4 | 9.1 | L | 87 | |

EXAMPLE X

A 450 ml capacity reactor with glass liner was charged with a mixture of dicobalt octacarbonyl (12.0 mmole Co, 2.052 g), triethylsilane (24.0 mmole Si, 2.790 g) and paraformaldehyde (0.1 mole, 3.0 g) in toluene (15.0 g). The mixture was flushed with nitrogen, the reactor sealed, flushed with synthesis gas, pressured to 2700 psig with CO/H$_2$ (1 2) and heated to 160° C. with agitation. After four hours, the reactor was allowed to cool, the gas pressure (1900 psig) noted, and the excess gas sampled and vented, 22.1 g of a two-phase liquid product was recovered, there was no solid precipitate at this stage.

Analysis (glc) of the more dense liquid product (3–4 ml) showed it to contain:
36.8 wt % ethylene glycol (EG)
7.1 wt % ethylene glycol monomethyl ether (EGMME)
2.4 wt % propylene glycol (PG)
8.2 wt % diethylene glycol (DEG)
18.3 wt % methanol
0.6 wt % ethanol
14.0 wt % water Analysis of the lighter liquid product (25 ml) showed it to contain:
91% toluene
1.0% methanol
0.5% ethylene glycol
0.9% ethylene glycol monomethyl ether Analysis of the typical gas sample showed it to contain:
67% hydrogen
32% carbon monoxide
0.1 methane The ethylene glycol product and its derivatives may be recovered from the crude, aqueous rich phase of the liquid product by fractional distillation in vacuo.

2. The process of claim 1, wherein the molar ratio of cobalt-to-silicon for the cobalt-containing compound and the silicon-containing promoter is in the range from 1:0.1 to 1:10.

3. The process of claim 1, wherein the cobalt-containing compound is selected from the group consisting of cobalt oxides, cobalt salts of a mineral acid, cobalt salts of a carboxylic acid and cobalt carbonyl or hydrocarbonyl derivatives.

4. The process of claim 3, wherein the cobalt-containing compound is from the group consisting of dicobalt octacarbonyl, cobalt(II) oxide, cobalt(II) nitrate, cobalt(II) acetate or cobalt acetylacetonate.

5. The process of claim 4, wherein the cobalt-containing compound is dicobalt octacarbonyl.

6. The process of claim 1, wherein the silicon-containing promoter is selected from the group consisting of triethylsilane, triphenylsilane, hydroxytriphenylsilane, diphenylsilane, tricyclohexylsilane and tetramethylsilane.

7. The process of claim 6, wherein the silicon-containing promoter is selected from the group consisting of triethylsilane, triphenylsilane and hydroxytriphenylsilane.

8. The process of claim 1, wherein the temperature is between 50° C. and 350° C.

9. The process of claim 1, wherein the temperature is between about 100° C. and 220° C.

10. The process of claim 1, wherein the pressure is between 1000 psi and 5000 psi.

11. The process of claim 1 wherein the aromatic hy-

TABLE I

SYNTHESIS OF ETHYLENE GLYCOL

| Example | Catalyst Precursor[a] and Solvent | Liquid Product Composition (Wt. %) | | | | | | | | Product Phase[b] | Proportion Total Liquid Product (%) | Liquid Yield Increase (%) |
|---|---|---|---|---|---|---|---|---|---|---|---|---|
| | | H$_2$O | MeOH | EtOH | EGMMe | EG | PG | DEG[c] | Solvent | | | |
| XI | Co$_2$(CO)$_8$Et$_3$SiH | 18.2 | 16.3 | 0.6 | 11.5 | 29.0 | 2.1 | 8.5 | | H | 11 | 9 |
| | m-Xylene | 0.9 | 1.1 | | 0.4 | 0.1 | | 0.1 | 90 | L | 89 | |
| XII | Co$_2$(CO)$_8$Et$_3$SiH | 35.1 | 16.4 | 0.8 | 6.9 | 24.5 | 1.8 | 3.0 | | H | 12 | 5 |
| | Tetralin | 0.6 | 0.3 | | 0.1 | 0.1 | 0.1 | | 94 | L | 88 | |
| XIII | Co$_2$(CO)$_8$Et$_3$SiH | 27.5 | 16.0 | 0.3 | 6.5 | 31.2 | 1.8 | 4.9 | 2.8 | H | 12 | 4 |
| | p-Xylene | 0.5 | 0.5 | | 0.2 | 0.1 | | | 93 | L | 88 | |
| XIV | Co$_2$(CO)$_8$Et$_3$SiH | 31.7 | 6.6 | 0.4 | 5.4 | 24.5 | 2.2 | 4.5 | 1.1 | L | 20 | 8 |
| | 1,2,4-Trichlorobenzene | | 0.2 | | 0.3 | | | | 91 | H | 80 | |
| XV | Co$_2$(CO)$_8$Ph$_3$SiH | 36.8 | 5.7 | 0.3 | 6.2 | 26.8 | 2.4 | 7.1[d] | [d] | L | 7 | 8 |
| | o-Dichlorobenzene | 1.0 | 1.5 | 0.1 | 5.6 | 1.2 | 0.8 | | 82 | H | 93 | |

[a]Reactor Charge: Co, 12.0 mmole; Ge, 6.0 mmole; Si, 24.0 mmole; (HCO)$_n$, 100 mmole; Solvent, 15.0 g
Run Conditions: 160° C., 2700 psi CO/H$_2$ (1:2) Initial Pressure, 4 hours
[b]Product Phase: L, lower density phase; H, higher density phase
[c]DEG fraction also contains alkyl silane
[d]DEG, o-Dichlorobenzene not resolved
[e]PG, Chlorobenzene not resolved

What is claimed is:

1. A low pressure process for making ethylene glycol comprising reacting synthesis gas, a mixture of carbon monoxide and hydrogen, plus formaldehyde or paraformaldehyde in the presence of a catalyst containing an effective amount of cobalt-containing compound, a a halogen-free silicon-containing promoter containing at least one silicon-carbon bond per molecule, and a solvent selected from the group consisting of an aromatic hydrocarbon solvent, a halogenated aromatic-containing solvent and a solvent containing both the halogen and ether functions, at a temperature of at least 50° C. and a pressure of at least 500 psig, wherein the majority of said ethylene glycol product separates as a separate liquid phase from the cobalt catalyst-rich solvent phase.

drocarbon solvent is selected from the group consisting of toluene, m-xylene, p-xylene and tetralin.

12. The process of claim 1 wherein halogenated aromatic solvent is selected from the group consisting of 1,2,4-trichlorobenzene, o-dichlorobenzene, bromobenzene and p-dibromobenzene.

13. The process of claim 1 wherein the halogenated ether solvent is selected from the group consisting of p-bromoanisole, m-chloroanisole and brominated diphenyl oxide.

14. A process for making ethylene glycol from synthesis gas, i.e., a mixture of carbon monoxide and hydrogen, and formaldehyde or paraformaldehyde which comprises reacting said synthesis gas and formaldehyde in a catalyst containing an effective amount of cobalt carbonyl compound, a promoter selected from the group consisting of triethylsilane and triphenylsilane, solubilized in a solvent from the group consisting of aromatic hydrocarbons, halogen substituted aromatics and halogenated ethers at a temperature of from about 100° C. to 220° C. and a pressure of from about 1000 psi to 4000 psi.

15. A process for making ethylene glycol which comprises reacting a mixture of carbon monoxide and hydrogen plus formaldehyde or paraformaldehyde in the presence of a liquid catalyst comprising dicobalt octacarbonyl coupled with a triethylsilane promoter solubilized in an aromatic solvent at a temperature of about 160° C. and a pressure of about 2700 psi, wherein the solvent is selected to maintain the cobalt catalyst in liquid phase and the ethylene glycol product forms a separate liquid phase from the cobalt catalyst-rich solvent phase.

* * * * *